(12) United States Patent
Arndt et al.

(10) Patent No.: US 10,258,031 B2
(45) Date of Patent: Apr. 16, 2019

(54) RECOVERY ASSEMBLY FOR CRYOPRESERVATION APPLICATIONS

(71) Applicant: Sanofi-Aventis Deutschland GmbH, Frankfurt am Main (DE)

(72) Inventors: Petra Arndt, Frankfurt am Main (DE); Volker Derdau, Frankfurt am Main (DE); Verena Siefke-Henzler, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 14/908,182

(22) PCT Filed: Aug. 5, 2014

(86) PCT No.: PCT/EP2014/066792
§ 371 (c)(1),
(2) Date: Jan. 28, 2016

(87) PCT Pub. No.: WO2015/018817
PCT Pub. Date: Feb. 12, 2015

(65) Prior Publication Data
US 2016/0165881 A1 Jun. 16, 2016

(30) Foreign Application Priority Data

Aug. 8, 2013 (EP) .................................... 13179685

(51) Int. Cl.
*B01L 3/00* (2006.01)
*A01N 1/02* (2006.01)

(52) U.S. Cl.
CPC ......... *A01N 1/0263* (2013.01); *A01N 1/0236* (2013.01); *A01N 1/0257* (2013.01);
(Continued)

(58) Field of Classification Search
CPC .................................................... B67C 3/2637
See application file for complete search history.

(56) References Cited

U.S. PATENT DOCUMENTS

| 4,108,338 A | * | 8/1978 | Howland | ............... B30B 15/304 |
| | | | | 222/286 |
| 4,205,598 A | * | 6/1980 | Leuschner | .......... A47J 31/0573 |
| | | | | 99/307 |

(Continued)

FOREIGN PATENT DOCUMENTS

| JP | S56-53701 | 5/1981 |
| JP | 2005-227076 | 8/2005 |

(Continued)

OTHER PUBLICATIONS

Form PCT/IB/373, International Preliminary Report on Patentability dated Feb. 9, 2016.
(Continued)

*Primary Examiner* — Jyoti Nagpaul
(74) *Attorney, Agent, or Firm* — Fish & Richardson P.C.

(57) ABSTRACT

The present invention relates to a recovery assembly for a cooling agent in a cryopreservation device, the recovery assembly comprises a cone-shaped funnel assembly comprising a support for mounting the funnel assembly to an access opening of a container to be at least partially filled with a cooling agent.

23 Claims, 3 Drawing Sheets

(52) U.S. Cl.
CPC ........... *B01L 3/56* (2013.01); *B01L 2200/023* (2013.01); *B01L 2200/025* (2013.01); *B01L 2200/028* (2013.01); *B01L 2200/0615* (2013.01); *B01L 2300/0609* (2013.01); *B01L 2300/1883* (2013.01)

(56) References Cited

U.S. PATENT DOCUMENTS

| | | | |
|---|---|---|---|
| 7,021,198 B1 * | 4/2006 | Lyall, III | A47J 31/0642 426/77 |
| 7,544,953 B2 * | 6/2009 | Goodman | B01L 3/0275 250/304 |
| 8,709,797 B2 * | 4/2014 | Woods | A01N 1/02 422/570 |
| 8,925,334 B2 | 1/2015 | Zimmermann et al. | |
| 2006/0156753 A1 | 7/2006 | Fuhr et al. | |

FOREIGN PATENT DOCUMENTS

| | | |
|---|---|---|
| JP | 2010-172868 | 8/2010 |
| JP | 2010-223283 | 10/2010 |
| WO | 02053967 A1 | 7/2002 |
| WO | 2010057589 A1 | 5/2010 |

OTHER PUBLICATIONS

Anonymous: "Handling, Transport and Storage of Cryogens", Department of Chemistry—Guidelines (University of Wollongong), Sep. 5, 2007 (Sep. 5, 2007), XP055096818, Retrieved from the Internet: URL:http://www.uow.edu.au/content/groups/public/@web/@sci/@chem/documents/doc/uow016882.pdf.

Japanese Office Action in Application No. 2016-532662, dated May 15, 2018, 3 pages.

* cited by examiner

RECOVERY ASSEMBLY FOR CRYOPRESERVATION APPLICATIONS

CROSS REFERENCE TO RELATED APPLICATIONS

The present application is a U.S. National Phase Application pursuant to 35 U.S.C. § 371 of International Application No. PCT/EP2014/066792 filed Aug. 5, 2014, which claims priority to European Patent Application No. 13179685.6 filed Aug. 8, 2013. The entire disclosure contents of these applications are herewith incorporated by reference into the present application.

FIELD OF INVENTION

The present invention relates to a recovery assembly and to a cryopreservation device for reducing consumption and losses of a cooling agent usable for cryopreservation of cryosamples. The invention therefore relates to an assembly and to a respective device for treating or examining of cryosamples and well as for inserting or extracting of cryosamples to and from a sample container.

BACKGROUND

Freezing of samples of e.g. biological material while maintaining the vitality of the sample material at temperatures of liquid nitrogen, i.e. −196° Celsius, is widely known in the areas of biology, pharmacology, medicine and biotechnology. Samples to be frozen and being designated as cryosamples are customarily stored and transferred in sample containers. Such sample containers, also denoted as cryotanks are typically filled with liquid nitrogen. Furthermore, such containers are thermally insulated and may resemble or comprise a so called Dewar vessel.

Insertion and extraction or removal of samples into and from such containers is sometimes critical. Especially when removing or extracting a sample from a filled sample container, a non-negligible amount of nitrogen may be spilled or may otherwise leave the container in a rather uncontrolled way. It is not only, that the cooling agent is spilled or wasted but that the surrounding air becomes enriched with gaseous nitrogen. Hence, there may further evolve a certain risk of health or of suffocating.

Document US 2006/0156753 A1 relates to the aspect of preventing a contact of the surrounding and relatively moist air when handling samples and/or sample containers. There, prevention of ice formation on the sample containers and/or samples and their germination is prevented in various ways. It is suggested to provide a protective container that receives the sample and/or the entire sample container during the handling. Moreover, a climate control equipment is provided which is connected to the protective container in order to dry and cool the ambient gas present in the protective container and/or replace it with the protective gas. Hence, an artificial atmosphere is preferably created in the protective container to prevent ice formation on the sample and/or sample container.

Complexity of the technical equipment to provide such a protective atmosphere is rather high as well as cost intensive.

It is therefore an object of the present invention to provide an improved cryopreservation device together with a recovery assembly for reducing and preventing uncontrolled escapement of the cooling agent. Moreover, consumption and waste of the cooling agent should be kept on a low or at least moderate level. It is a further aim to enhance operational safety of such devices and to protect operative staff against uncontrolled and vast exposure to the cooling agent, e.g. liquid nitrogen.

SUMMARY

In a first aspect, a recovery assembly for a cryopreservation device is provided. The recovery assembly comprises a cone-shaped funnel assembly with a support. The recovery assembly is particularly adapted and operable to recover a cooling agent of the cryopreservation device. By means of the support the funnel assembly and hence the entire recovery assembly can be mounted on or to an access opening of a container, typically of a cryopreservation container or sample container at least partially to be filled with a cooling agent, e.g. liquid nitrogen. The container may comprise a Dewar vessel being open to the top in order to allow permanent evaporation cooling of the liquid cooling agent disposed therein. The recovery assembly is adapted to be mounted to the upper access opening of the container for recovery of the cooling agent, especially when extracting a sample from the container.

The recovery assembly further comprises at least one cone-shaped funnel portion converging towards the support. Hence, the recovery assembly may comprise a funnel of e.g. circular-shape or circular cross section extending in a diverging way from the support. By means of the cone-shaped funnel portion, excess cooling agent, which in the course of extraction of a cryosample may drip or rinse down from a sample or from a respective specimen holder can be collected and fed back into the container in a controlled way.

In this way, the recovery assembly helps to save and to reduce consumption of a cooling agent and allows for an easy and efficient draining of the cooling agent back into the sample container in the event of extraction or removal of a specimen holder therefrom which is equipped with one or several cryosamples.

In a preferred embodiment, the support of the recovery assembly is adapted to receive an upper neck portion and/or an upper rim of the container. The container which typically comprises a Dewar vessel may be cone-shaped towards it upper, distal end. This way, an upper rim or an upper end of said container may be received in the support of the recovery assembly, which may be integrally formed with the recovery assembly's funnel assembly. In a rather basic embodiment, the support may coincide with a lower edge of the funnel assembly, hence a lower edge of a cone-shaped sidewall portion of the funnel assemble may form the support.

Preferably, the support of the recovery assembly and the upper neck portion of the sample container are correspondingly shaped so as to allow a well defined mutual and releasable assembly of recovery assembly and sample container.

The support to be mounted to the access opening of the container is preferably mechanically engageable with said container. In particular, the support and the access opening comprise a fastening, typically in form of mutually engaging fixing means, such like positive engaging locking means, a bayonet cap, a screw connection or mutually engaging bolts and recesses. This way, a reliable and durable mutual fastening and interconnection of the recovery assembly and the sample container can be established.

According to another embodiment the funnel assembly further comprises a blind assembly extending across the inner cross-section of the funnel assembly. By means of the blind assembly, the effective size of an access opening or through opening of the funnel assembly can be modified in order to decrease or increase the size of the through opening. This way, a thermal exchange with the environment and hence a rate of evaporation of the cooling agent can be regulated. Moreover, by means of the blind assembly a vapor penetrable closure can be provided for the sample container. This way, the access opening of the container can be effectively protected against ingress of external substances, particles or items, which may otherwise accidentally enter the probe container. At the same time, the blind assembly does not hinder evaporation cooling of the cooling agent.

By means of the variable blind assembly the safety for operational staff working with the cooling agent can be increased. Moreover, by means of the blind assembly the amount of gaseous cooling agent and the amount of liquid cooling agent in the surrounding environment can be kept on a comparatively low level. This way, a risk of burning and suffocation for an operator can be advantageously reduced.

In a further preferred embodiment the blind assembly provides and comprises a through opening, which when assembled to the sample container substantially flushes with the access opening of said container. The through opening of the blind assembly is of variable size and is modifiable by an operator on demand. If the operator intends to extract or to store a specimen holder or a cryosample from or into the sample container, the through opening of the blind assembly can be at least temporarily increased. In a storage mode, wherein the at least one specimen holder together with numerous cryosamples is only to be kept and immersed in the liquid cooling agent, the size of the blind assembly's through opening can be reduced to a minimum in order to reduce evaporation and escapement of the cooling agent.

In a further preferred embodiment the blind assembly comprises an iris blind to modify the size of its through opening. Moreover, iris blind mechanisms are widely distributed and are commercially available, e.g. in the field of optics.

In a further preferred embodiment, the blind assembly, in particular the iris blind assembly is integrated into the funnel assembly of the recovery assembly. Preferably, an actuation member operable to modify the size of the iris blind's through opening is accessible from outside the funnel assembly. In particular, the actuation member extends radially outwardly from the funnel assembly. With this integral embodiment, the iris blind assembly is preferably arranged gas and/or liquid tight in the funnel assembly so that liquid cooling agent, which may eventually rinse down the inner sidewall of the funnel assembly is effectively hindered to leak through the iris blind assembly.

In a further preferred embodiment the funnel assembly comprises at least one outwardly extending recess at an inside wall portion, preferably located above the blind assembly, to receive and to support a specimen holder in an inclined orientation above the blind's through opening. The recess may comprise a slanted or inclined bottom portion in order to support the lifted specimen holder in the inclined orientation.

According to another embodiment the funnel assembly further comprises an additional support extending from an upper end thereof obliquely opposite to the outwardly extending recess. This way, a lifted specimen holder can be kept in supported and in an inclined orientation above an orifice of the support and/or above the blind assembly. The additional support is either displaceably or pivotably mounted at the upper edge of the funnel assembly. This way, the support can be oriented and positioned in a specimen-supporting configuration on demand. If not used or required the support can for instance be pivoted inwardly to but against the inner sidewall of the funnel assembly. Alternatively, the support may also be pivoted outwardly or may even be disconnected or dismounted from the funnel assembly.

The additional support may at least partially extend radially inwardly into the funnel assembly in order to provide a holding means and a holder for the inclined oriented specimen holder provided in the recess.

In a further preferred embodiment, the funnel assembly comprises a thermally insulated material and/or a thermally insulating structure. Hence, the funnel assembly is of non-thermoconducting material. In this way, operational safety of the recovery assembly can be further increased. Touching or handling of the funnel assembly may not harm the skin of an operator. Hence, the risk of burning can be substantially reduced.

In a further preferred embodiment, the recovery assembly is releasably attachable to the sample container. In particular, the support of the recovery assembly and the access opening of the sample container are releasably engageable. This way, the recovery assembly may be arbitrarily used with a large variety of sample containers. While cryosamples are stored in a specific container, the recovery assembly may be disassembled and may be used with other sample containers at least for extracting samples therefrom. Therefore, a single recovery assembly may be efficiently used with several sample containers. Here, it is beneficial when the recovery assembly and the sample container comprise or form a standardized mutual fastening to enable universal exchange of sample containers and recovery assemblies.

In still another embodiment the blind assembly further comprises an annular frame and multiple radially displaceable segments extending in the plane of the frame. The segments are typically displaceable in radial and eventually also in tangential or circumferential direction in order to modify or to vary the size of the blind's through opening.

It is even conceivable that the size of the blind's through opening can be reduced to such an extend that the through opening's cross section or diameter is smaller than the outer dimensions of the specimen holder. In this way, the substantially closed blind may even serve as a support structure for a lifted specimen holder. Especially when the segments of an iris blind provide a sufficient mechanical stability the lifted specimen holder can be put onto the substantially closed blind.

In such a configuration the at least one, preferably two oppositely located and radially inwardly pivoted additional supports extending radially inwardly from the upper edge of the funnel assembly are of advantage to keep the specimen holder in an upright orientation when standing on the closed blind.

In still another aspect the invention also relates to a cryopreservation device, which is adapted to store at least one specimen, in particular a cryosample. The cryopreservation device comprises a container to accommodate a liquid cooling agent, such as liquid nitrogen. Said container further comprises an access opening at a distal upper end. Moreover, the cryopreservation device comprises and is equipped with a recovery assembly as described above. Here, the recovery assembly is mounted on the access opening via its support or may be simply operable to be mounted to said access opening.

In a further and preferred embodiment, the recovery assembly is removably mounted on the access opening, preferably in a releasable and reconfigurable way. This allows to arbitrarily couple the recovery assembly with a variety of sample containers whenever specimens or cryosamples have to be put into or taken from the container.

According to a further embodiment the recovery assembly also comprises an extraction assembly at least for extracting a specimen, e.g. a cryosample from the container through the access opening. The extraction assembly of the recovery assembly is particularly adapted to grip and to raise at least one specimen out of the cooling agent and upwards through the access opening of the sample container.

The recovery assembly and the extraction assembly may either be releasably coupled or may be integrally formed. With a releasable coupling of recovery assembly and extraction assembly, the recovery assembly may be used with other, e.g. stationary and immobile extraction assemblies, which may for instance be mounted to a ceiling of a room. With an integrated arrangement of recovery assembly and extraction assembly, mounting of the recovery assembly on the access opening of the sample container immediately provides an appropriate position of the extraction assembly relative to the sample container. This way, a separate positioning and configuration of the extraction assembly is not required.

In a further embodiment, wherein the extraction assembly is attached to the recovery assembly, the extraction assembly may comprise at least one pillar or a similar support structure extending through the recovery assembly's funnel portion to support a pulling device located above an upper end of the funnel portion. The pulling device may comprise a flexible strap or a chain, by means of which the at least one specimen located in the sample container can be gripped and lifted out of the sample container.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, preferred embodiments of the invention will be described in greater detail by making reference to the drawings, in which.

DETAILED DESCRIPTION

Figure 1:
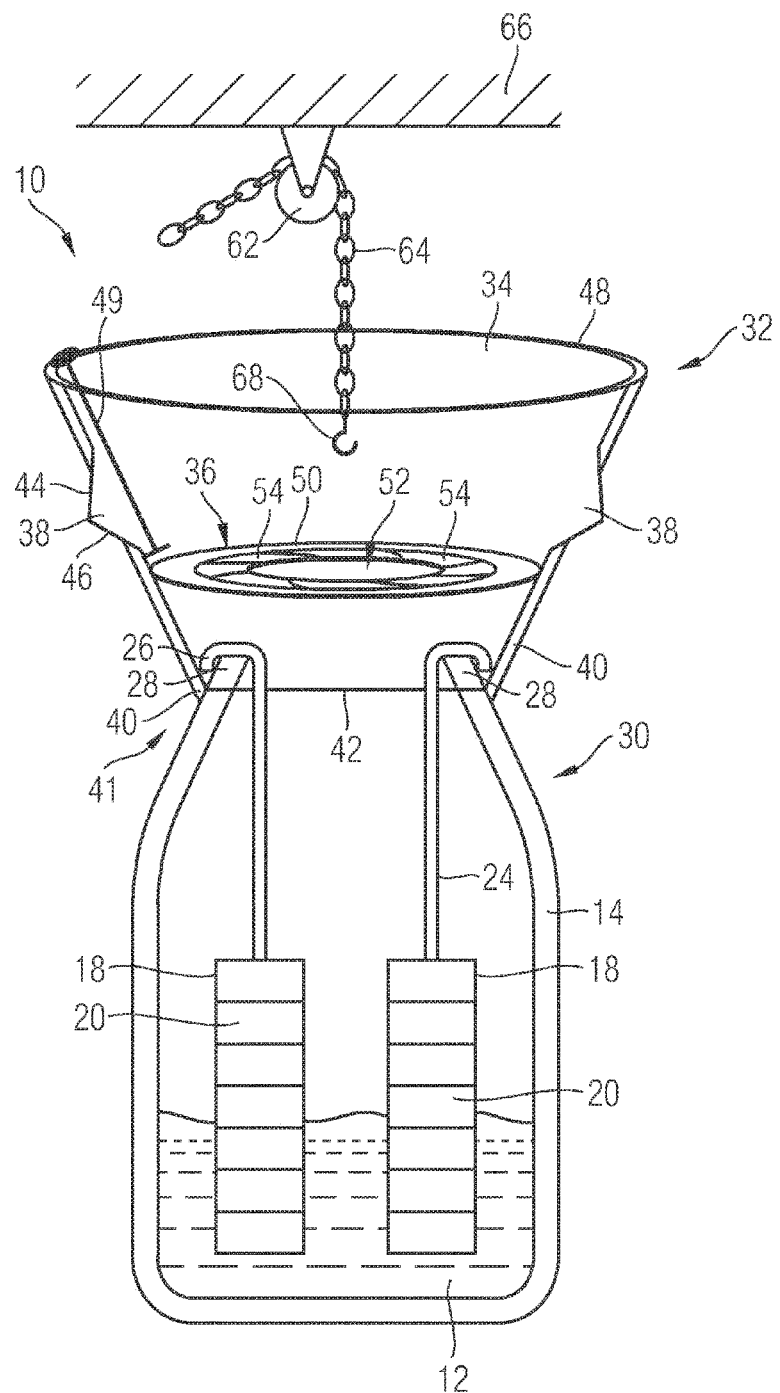
FIG. 1 schematically illustrates a cryopreservation device equipped with a recovery assembly in a storage configuration.
Figure 2:
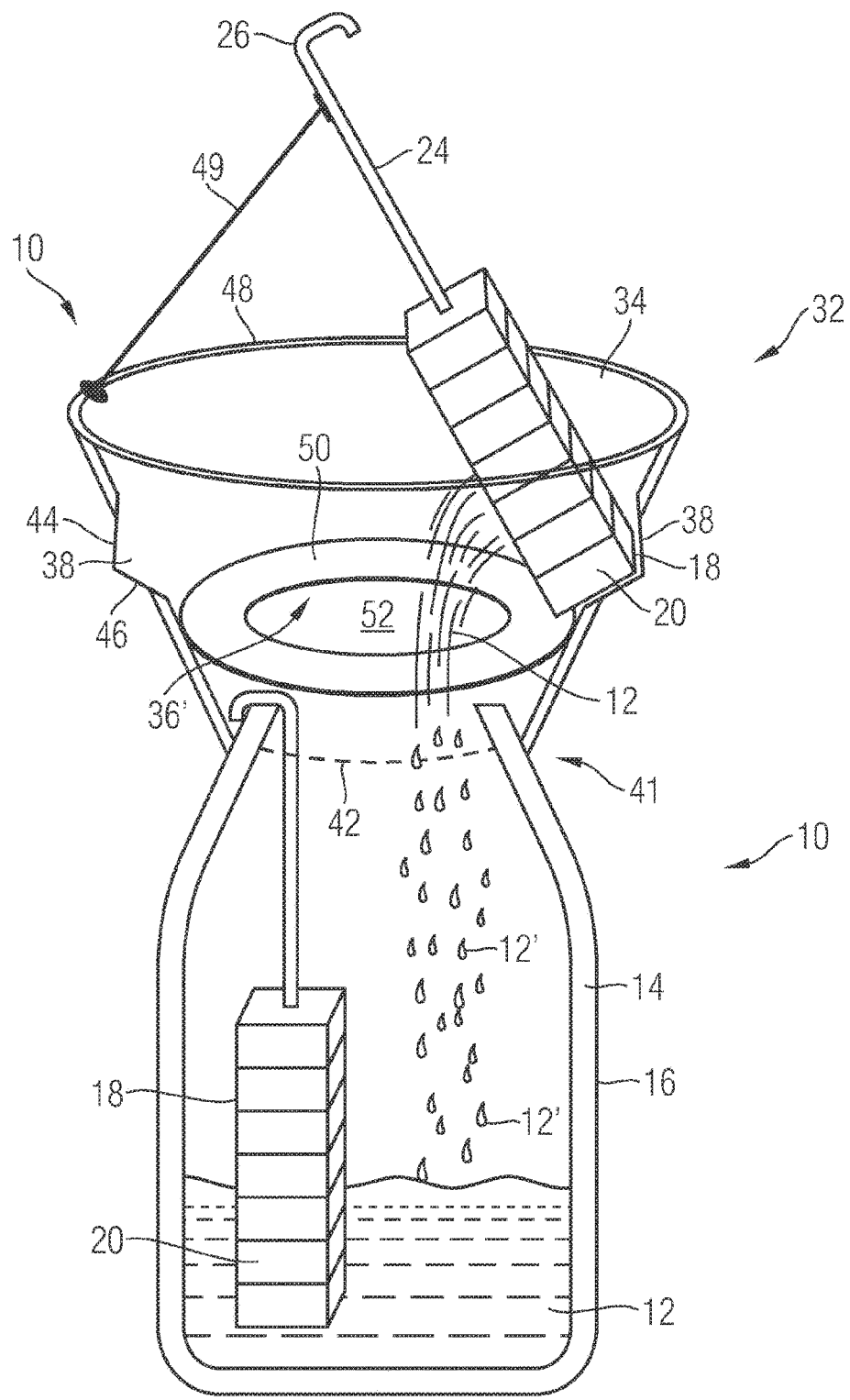
FIG. 2 shows the device according to FIG. 1 with a specimen holder extracted from the device, FIG. 3 schematically shows the iris blind assembly in a substantially closed configuration

The cryopreservation device 10 as shown in FIGS. 1 and 2 comprises a sample or storage container 16 typically designed as a Dewar vessel. The storage container 16 comprises a Dewar wall structure 14 which is substantially non-thermoconducting. Hence, the surrounding walls of the storage container 16 are thermally insulated.

The storage container 16 comprises a converging neck portion 30, which may resemble a bottleneck. At its upper end, the neck portion 30 comprises an annular rim 28, which in the embodiment according to FIGS. 1 and 2 serves to engage with a hook 26 of a hanger 24 interconnected with a specimen holder 18. The specimen holder 18 comprises numerous compartments or containers 20 to receive various cryosamples. In storage mode as illustrated in FIG. 1, the specimen holder 18 is intended to be completely immersed in the liquid cooling agent 12, typically comprising liquid nitrogen at −196° Celsius.

The cryopreservation device 10 is further equipped with a funnel assembly 32 comprising a cone-shaped funnel 34 which is to be assembled on top of an access opening of the neck portion 30 of the storage container 16. The funnel 34 comprises a support 40 with a lower edge 42 which may frictionally engage with the neck portion 30 of the storage container 16. The lower portion of the funnel 34 therefore provides a support structure 40 by way of which the funnel assembly 32 can be mounted on the storage container 16 in a well-defined way.

As indicated by reference numeral 41, the support structure 40 and the neck portion 30 may comprise a mutually corresponding fastening, e.g. in form of positive engaging locking means, such like a bayonet fixing, a screw connection or by means of mutually corresponding recesses and bolts or pins.

By means of the funnel assembly 32, raised and lifted specimen holders 18 can be oriented in an inclined way as illustrated in FIG. 2, thereby allowing to feed back excess cooling agent 12' into the storage container 16. Since the funnel 34 radially widens and radially diverges in an upward direction, liquid cooling agent 12 which may rinse down from the lifted specimen holder 18 can be collected over a comparatively large area compared to the size of the sample containers 16 access opening.

Furthermore and as illustrated in FIGS. 1 and 2, the funnel 34 also comprises radially outwardly extending notches or recesses 38 extending from an inner wall of the funnel 34. As shown in FIG. 2 the recesses 38 comprise a slanted or inclined bottom portion 46 and a respective sidewall portion 44. By means of the inclined bottom portion 46, the recesses 38 are operable to support a lifted specimen holder 18 in an inclined orientation above the blind assembly's 36 through opening 52.

When kept in an inclined orientation, excess cooling agent may drop or rinse down from various cryosample compartments 20 of the specimen holder 18 as shown in FIG. 2 in form of various drops 12'. Additionally, the recovery assembly can be provided with an additional support 49, which is for instance pivotally arranged by means of a hinge at an upper end or upper rim 48 of the funnel 34.

Such an additional support may be folded to extend at least partially radially inwardly in order to support, to hold and to stabilize the specimen holder 18 in an inclined orientation when leaned against the radially inwardly pivoted support. If not used the support 49 can either be pivoted radially inwardly to abut against an inside wall of the funnel assembly 32. Alternatively the support 49 may be pivoted radially outwardly for not obstructing the inside wall of the funnel assembly 32. Alternatively, the support 49 may be detachably or removably arranged at the upper rim 48.

Figure 3:
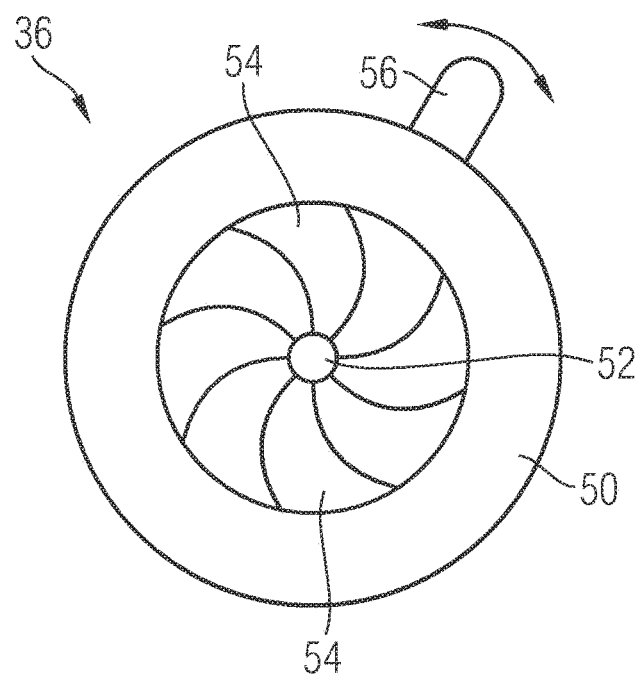
Figure 4:
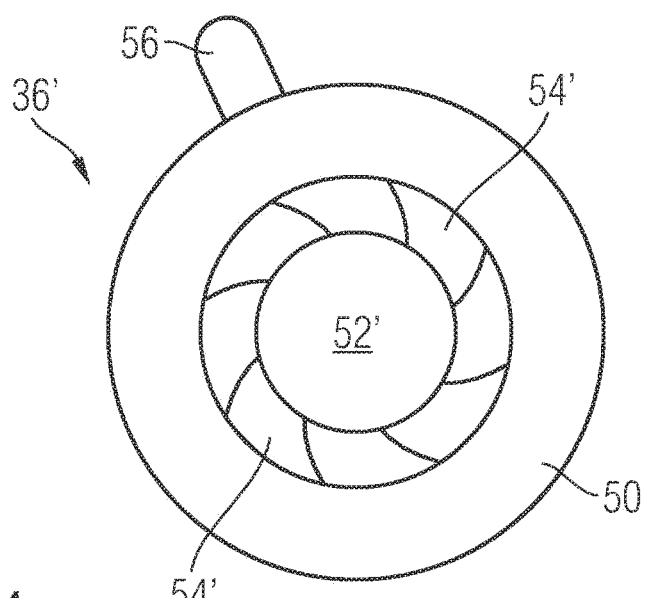
FIG. 4 shows the iris blind assembly in a substantially open configuration.

Additionally and as illustrated in FIGS. 1-4 the funnel assembly 32 further comprises an iris blind assembly 36 arranged above a lower edge 42 of the funnel 34 and extending across the entire funnel 34. The iris blind assembly 36 comprises an annular frame 50 and various iris segments 54 radially inwardly extending therefrom. The various iris segments 54 are radially and/or tangentially displaceable between at least two extreme configurations as shown in FIG. 3 and FIG. 4.

The various iris segments 54 are further operably connected and engaged with an actuation member 56 extending radially outwardly from the frame 50. By twisting or displacing the actuation member 56 from e.g. a 1 o'clock configuration as shown in FIG. 3 towards an 11 o'clock configuration as shown in FIG. 4, the various iris segments 54 can be simultaneously displaced radially outwardly in order to increase the size of the through opening 52 towards a maximum increased configuration as indicated in FIG. 4 with 52'. Even though not particularly illustrated the actuation member 56 of the iris blind assembly 36 preferably protrudes from the funnel 34 radially outwardly.

Only for reasons of simplicity, the various iris segments 54 are not separately illustrated in the sketch of FIG. 2. By means of the iris blind assembly 36 of variable size, the rate of evaporation of the liquid cooling agent 12 can be regulated and can be decreased. This way, contamination of the environment with evaporated or liquid cooling agent 12 can be reduced to a minimum, thereby enhancing operational safety and reducing the risk of burning or suffocating.

Furthermore and as illustrated in FIGS. 1 and 2, the funnel 34 also comprises radially outwardly extending notches or recesses 38 extending from an inner wall of the funnel 34. As shown in FIG. 2 the recesses 38 comprise a slanted or inclined bottom portion 46 and a respective sidewall portion 44. By means of the inclined bottom portion 46, the recesses 38 are operable to support a lifted specimen holder 18 in an inclined orientation above the blind assembly's 36 through opening 52. Here, the pivotable or removable support 49 is of particular use to keep a lifted specimen holder 18 in the inclined orientation.

Additionally, it is conceivable to put the lifted specimen holder 18 onto the closed iris blind assembly 36. The specimen holder may be lifted out of the storage container 16 when the iris blind is in an opened configuration. Thereafter the size of the through opening 52 of the iris blind assembly 36 can be reduced to such an extend that the diameter of the remaining through opening 52 is smaller than the cross section of the specimen holder 18. Then the specimen holder 18 can be positioned onto the segments of the iris blind assembly 36. In such a configuration the at least one support 49 or several supports 49 are operable to keep the specimen holder 18 in a stable orientation, e.g. in an upright or inclined configuration.

When kept in an inclined orientation either on the segments 54 of the iris blind assembly 36 or in the radially outwardly extending recess 38, excess cooling agent may drop or rinse down from various cryosample compartments 20 of the specimen holder 18 as shown in FIG. 2 in form of various drops 12'. Additionally but not illustrated here, the recovery assembly may be provided with an additional support, e.g. pivotally arranged by means of a hinge at an upper end or upper rim 48 of the funnel 34.

Such a support may be folded to extend at least partially radially inwardly in order to support, to hold and to stabilize the specimen holder 18 in an inclined orientation when leaned against the radially inwardly pivoted support.

Lifting of the specimen holder out of the storage container 16 can be provided either manually, e.g. by gripping the hanger 24 or hook 26 with the hands of operating personal. Alternatively or additionally and as illustrated in FIG. 1 an extraction assembly 60 can be provided, e.g. comprising a pulley 62 that serves as a deflection wheel for a chain 64 or for a comparable flexible strap. The chain may comprise a hook 68 to engage with a corresponding hook 26 provided at the upper end of the specimen holder 18.

As further shown in FIG. 1, the pulley 62 is mounted on a ceiling 66. By exertion of a lateral, sideward or even downward directed tensile load to the other free end of the chain 64, the specimen or specimen holder 18 can be lifted and can be raised above a level of an upper edge 48 of the funnel assembly 32. Alternatively, but not illustrated here, the pulley may be releasably mounted and fixed to the funnel assembly, e.g. by means of at least one, preferably two or three circumferentially distributed pillars extending upwardly from the funnel assembly in order to provide a support for the pulley 62.

The invention claimed is:

1. A recovery assembly for a cryopreservation device, comprising:
   a cone-shaped funnel assembly including an angled sidewall having a first end and a second end, the funnel assembly comprising:
   a support for mounting the first end of the angled sidewall of the funnel assembly to an access opening of a cryopreservation container to be at least partially filled with a cooling agent; and
   at least one outwardly extending recess positioned between the first end and the second end of the funnel assembly, wherein the at least one outwardly extending recess comprises an inclined bottom portion and a side wall portion each extending outwardly in a direction away from the angled sidewall to support a specimen holder in an inclined orientation above the access opening of the container.

2. The recovery assembly according to claim 1, wherein the support is adapted to receive an upper neck portion and/or an upper rim of the container.

3. The recovery assembly according to claim 1, wherein the funnel assembly further comprises a blind assembly extending across the inner cross-section of the funnel assembly.

4. The recovery assembly according to claim 3, wherein the blind assembly provides a through opening of variable size.

5. The recovery assembly according to claim 3, wherein the blind assembly comprises an iris blind.

6. The recovery assembly according to claim 3, wherein an actuation member of the blind assembly extends outside or from an outer circumference of the funnel assembly.

7. The recovery assembly according to claim 3, wherein the at least one recess is located above the blind assembly.

8. The recovery assembly according to claim 1, further comprising an additional support extending from an upper end of the funnel assembly obliquely opposite to the outwardly extending recess.

9. The recovery assembly according to claim 1, wherein the funnel assembly comprises a thermally insulated material and/or a thermally insulated structure.

10. The recovery assembly according to claim 1, wherein the support is releasably attachable to the access opening of the container.

11. The recovery assembly according to claim 3, wherein the blind assembly comprises an annular frame and multiple radially displaceable segments extending in the plane of the frame.

12. The recovery assembly according to claim 1, further comprising:
    a through opening of variable size positioned between the at least one outwardly extending recess and the access opening.

13. A cryopreservation device for storing of at least one specimen, the device comprising:
    a container to accommodate a liquid cooling agent wherein said container comprises an access opening at a distal upper end, and
    a cone-shaped funnel assembly including an angled sidewall having a first end and a second end, wherein the first end of the cone-shaped funnel assembly is mounted on the access opening via a support, wherein the cone-shaped funnel assembly includes at least one outwardly extending recess positioned between the first end and the second end of the funnel assembly, wherein the at least one outwardly extending recess comprises an inclined bottom portion and a side wall portion each extending outwardly in a direction away from the angled sidewall to support a specimen holder in an inclined orientation above the recess opening of the container.

14. The cryopreservation device according to claim 13, wherein the recovery assembly is removably mounted on the access opening of the container.

15. The cryopreservation device according to claim 13, wherein the container comprises a Dewar vessel.

16. The cryopreservation device according to claim 15, wherein the Dewar vessel is cone-shaped towards an upper end.

17. The cryopreservation device according to claim 13, wherein the container comprises a Dewar wall structure which is substantially non-thermoconducting.

18. A recovery assembly for a cryopreservation device, comprising:
   a cone-shaped funnel assembly comprising:
   a support for mounting the funnel assembly to an access opening of a cryopreservation container to be at least partially filled with a cooling agent; wherein the funnel assembly further comprises a blind assembly extending across the inner cross-section of the funnel assembly and wherein the blind assembly comprises an iris blind, wherein the iris blind comprises an annular frame and various iris segments radially inwardly extending therefrom and being radially displaceable relative to the annular frame.

19. The recovery assembly according to claim 18, wherein the blind assembly provides a vapor penetrable closure for the cryopreservation container.

20. A cryopreservation device for storing of at least one specimen, the device comprising:
   a container to accommodate a liquid cooling agent wherein said container comprises an access opening at a distal upper end, and
   a recovery assembly according claim 18, wherein the recovery assembly is mounted on the access opening via its support.

21. The cryopreservation device according to claim 20, wherein the container comprises a Dewar vessel.

22. The cryopreservation device according to claim 20, wherein the container comprises a Dewar wall structure which is substantially non-thermoconducting.

23. The cryopreservation device according to claim 20, wherein the Dewar vessel is cone-shaped towards an upper end.

* * * * *

UNITED STATES PATENT AND TRADEMARK OFFICE
CERTIFICATE OF CORRECTION

PATENT NO. : 10,258,031 B2
APPLICATION NO. : 14/908182
DATED : April 16, 2019
INVENTOR(S) : Petra Arndt, Volker Derdau and Verena Siefke-Henzler Page 1 of 1

It is certified that error appears in the above-identified patent and that said Letters Patent is hereby corrected as shown below:

In the Claims

In Column 10, Line 15, Claim 20, after "according" insert -- to --

Signed and Sealed this
Twenty-fifth Day of June, 2019

Andrei Iancu
*Director of the United States Patent and Trademark Office*